United States Patent [19]

Tabuchi et al.

[11] 4,391,908

[45] Jul. 5, 1983

[54] METHOD FOR PRODUCING CITRIC ACIDS

[75] Inventors: Takeshi Tabuchi; Matazo Abe, both of Tokyo, Japan

[73] Assignee: Takeda Chemical Industries, Ltd., Osaka, Japan

[21] Appl. No.: 916,262

[22] Filed: Jun. 16, 1978

Related U.S. Application Data

[63] Continuation of Ser. No. 783,740, Dec. 13, 1968, abandoned, which is a continuation-in-part of Ser. No. 735,199, Jun. 7, 1968, abandoned.

[30] Foreign Application Priority Data

Jun. 7, 1967 [JP] Japan .................................. 52-36391
Dec. 13, 1967 [JP] Japan .................................. 52-79802

[51] Int. Cl.³ .......................... C12P 7/48; C12N 1/28; C12R 1/72; C12R 1/73; C12R 1/74
[52] U.S. Cl. .................................. 435/144; 435/249; 435/921; 435/923; 435/924
[58] Field of Search ......................................... 435/144

[56] References Cited

U.S. PATENT DOCUMENTS 3,489,648  1/1970  Wegner ............................... 435/248

OTHER PUBLICATIONS

Klug et al., *Applied Microbiology*, 15:690, (1967).
Tanaka, et al.: "Study on Citric Acid Fermentation by Yeast (The Fourth Report)", *Agri. Chem. Soc. Jap.*, (Mar. 15, 1967).
Tabuchi, et al., (Tabuchi I), "Study on Citric Acid Fermentation by Yeast (First Report)"; *Agri. Chem. Soc. Jap.*, (1965).
Tabuchi et al., (Tabuchi II), "Study on Fermentation of Citric Acid by Yeast (Second Report)", *Agri. Chem. Soc. Jap.* (1966).
Tabuchi et al., (Tabuchi III), "Study on Fermentation of Citric Acid by Yeast (Third Report)", *Agri. Chem. Soc. Jap.*, (1966).
Komagata et al., *J. Gen. Appl. Microbiol.*, 10:313, (1964).
Otsuka et al., *J. Gen. Appl. Microbiol.*, 12:1, (1966).
Arimi et al., *Agr. Biol. Chem.*, 29:1004, (1965).
Takeda et al., *Agr. Biol. Chem.*, 29:796, (1965).
Takahashi et al., *Agr. Biol. Chem.*, 29:292, (1965).
Ertola et al., *Biotechnol. Bioeng.* VIII: 309, (1965).
Miller, et al., *Biotechnol. Bioeng.* VI: 299, (1964).
Miller et al., *Biotechnol. Bioeng.*, VIII: 549, (1966).
Miller, et al., *Biotechnol. Bioeng.* VIII: 567, (1966).
Johnson, *Chem. & Industry*, 1532, (Sep. 5, 1964).
Dagley, *Methods of Enzymatic Analysis*, p. 313 et seq, (1963).
Siebert, *Method of Enzymatic Analysis*, p. 318 et seq., (1963).

*Primary Examiner*—Lionel M. Shapiro
*Attorney, Agent, or Firm*—David G. Conlin; Sewall P. Bronstein

[57] ABSTRACT

Citric acids are produced by culturing a citric acids-accumulating and hydrocarbon-assimilating strain of a yeast of the genus Candida in an aqueous medium containing, as main carbon source, at least one normal paraffin with from 9 to 20 carbon atoms, inclusive, in the molecule, at a specific pH, and recovering accumulated citric acids from the culture broth.

34 Claims, No Drawings

METHOD FOR PRODUCING CITRIC ACIDS

This application is a continuation of our application Ser. No. 783,740, filed Dec. 13, 1968, now abandoned, which application was a continuation-in-part of our application Ser. No. 735,199, filed Jun. 7, 1968, now abandoned.

This invention relates to a method for producing citric acid and/or (+)-isocitric acid ("citric acid and/or (+)-isocitric acid" are generally referred to as "citric acids" in this specification unless otherwise mentioned). More specifically, this invention relates to a method for producing citric acids, which comprises inoculating a citric acids-accumulating and hydrocarbon-assimilating strain of a yeast belonging to the genus Candida in an aqueous culture medium containing, as the main carbon source, at least one normal paraffin containing 9 to 20 carbon atoms, inclusive, in the molecule, incubating the culture at a specific pH; and recovering the accumulated citric acids therefrom.

Citric acids are in great demand and are used, for example, as an acidulant in beverages and in pharmaceutical sirups. The present inventors have found that various yeasts have the ability of accumulating citric acids in a medium containing such carbon sources as glucose, sucrose, etc. and on this basis completed a method for the production of citric acids. However, this method requires the relatively expensive carbohydrates as the carbon sources and generally results also in the production of polyhydric alcohols, thus resulting in a low yield of the desired citric acids.

In an attempt to overcome these disadvantages, the present inventors have further found that there exist citric acids-accumulating and hydrocarbon-assimilating strains of yeasts, that most of these yeasts belong to the genus Candida, that a suitable pH control of the culture medium during the incubation enables the strains to accumulate citric acids abundantly, and that the yield is high and, thus, recovery is easily carried out.

The main object of the present invention is to provide a method for producing citric acids from relatively inexpensive carbon sources in a good yield.

This object is realized by incubating a yeast which is capable of utilizing hydrocarbons, as sole carbon source, particularly normal paraffins with 9 to 20 carbon atoms, inclusive, in the molecule and which is also capable of accumulating citric acids in a medium containing one or more of the said hydrocarbons.

In the method of the present invention, any yeast is employed as long as it is capable of utilizing the hydrocarbons mentioned above and of accumulating citric acids. However, yeasts belonging to the genus Candida are most favorably applied to the present method.

The microbial characteristics of yeasts are not generally fixed and this applies also to the characteristics of those belonging to the genus Candida. Otherwise stated, there are many mutants and variants, and among the mutants and variants, regardless of whether the variation is caused naturally or artificially, for example, with X-ray, ultraviolet ray, or by the action of chemical reagents, any one of these can be employed in the method of the present invention as long as it is hydrocarbon-assimilating and citric acids-accumulating.

The culture medium to be employed in this invention is required to contain at least one normal paraffin with 9 to 20 carbon atoms, inclusive, in the molecule, for example, nonane, decane, dodecane, tetradecane, hexadecane, octadecane and eicosane. There may also be exemplified such impure materials as kerosene, heavy paraffins, heavy gas oil, gas oil, etc., each containing at least about 10% (volume/volume) of normal paraffins with 9 to 20 carbon atoms in the molecule. The hydrocarbons are generally used in such an amount as to make the concentration in the culture medium of the normal paraffin(s) with 9 to 20 carbon atoms in the molecule, as a whole about 3 to 20% (volume/volume) in the culture medium.

As these hydrocarbons are scarcely soluble in water, the addition thereof to an aqueous culture medium is practically carried out under stirring or shaking to prepare a suspension containing very fine particles. If desired, a suspending agent, e.g. a surfactant of the type of polyoxyethylene sorbitan monostearate can be employed.

These hydrocarbons are by themselves sufficient carbon sources, but, if desired, commonly employable carbon sources such as carbohydrate (e.g. glucose) can be used together with the hydrocarbons.

As digestible nitrogen sources, there are exemplified such inorganic nitrogen compounds as ammonium chloride, ammonium sulfate, ammonium phosphate, etc., such organic nitrogen compounds as ammonium acetate, peptone, urea, yeast extract, corn steep liquor, etc. When organic nitrogen compounds or materials are employed, they may be consumed not only as nitrogen sources but also as a part of the carbon sources.

Further, a small quantity of inorganic salts such as sodium chloride, phosphates, salts of metals such as calcium, zinc, iron, magnesium, etc. can be added to the medium and, if necessary, conventional nutrient factors or antifoaming agents such as vitamins, animal oil, vegetable oil or mineral oil, can also be added.

In carrying out the process of this invention, it is preferable to employ a liquid culture medium, and the incubation is carried out aerobically, i.e. with aeration under static or submerged conditions.

Incubation conditions such as the pH of the medium and the incubation temperature should be controlled so that the objective citric acids are accumulated in the maximum amount. The pH of the culture is maintained between about 4 and about 7.5, more advantageously between 5 and 6.5.

As the pH goes down in the course of incubation, the addition of salts of an alkali metal, an alkaline earth metal or of ammonium, as well as the corresponding bases, as pH-adjusting agents is recommendable in order to keep the pH in an optimal range. The salts or bases include, for example, calcium carbonate, calcium acetate, sodium hydroxide, calcium hydroxide, aqueous ammonia, etc. Addition of these is effected before or at the start of the cultivation or at a suitable stage in the course of the cultivation, and in the former case, salts are more desirably employed.

Generally, calcium ion as well as magnesium ion promotes the accumulation of citric acids. The incubation is carried out at a temperature between about 15° and about 40° C., advantageously at a temperature between about 20° and about 30° C.

Thus-accumulated citric acids in the culture broth are recovered therefrom by applying per se conventional means such as filtration, centrifugation, heating, column chromatography, activated carbon treatment, concentration, sedimentation, etc., solely or in combination. If case demands, the pH of the culture broth is adjusted. By way of illustration, when there exists insoluble calcium citrates in the culture broth, it is desirable to acidify the broth with hydrochloric acid to solubilize the said salts, followed by further separation procedures.

If desired, after being separated from yeast cells, the culture liquid is neutralized with sodium hydroxide, calcium carbonate, milk of lime, or the like. Thus-obtained solution is kept standing at room temperature or under heating followed by filtration or centrifugation and drying to give calcium citrates as white powder. The powder is, if needed, further purified by per se conventional means such as neutralization, etc.

If the powder is a mixture of citric acid and (+)-isocitric acid and the mixture is desired to be separated into each acid, the separation may be effected, for instance by the following means:

The powder dissolved in hot water is subjected to suction-filtration, while hot, to obtain calcium salts of citric acids, followed by neutralization and filtration.

The filtrate is concentrated to a sirup state, and then subjected to column chromatography on silica gel utilizing an n-butanol-chloroform mixture as an eluting solvent, whereby citric acid and (+)-isocitric acid flow down into different fractions.

Citric acid and (+)-isocitric acid are respectively measured by pentabromoacetone method (Seikagaku, 27 72 (1955) and by enzymatic method (Methods of Enzymatic Analysis (Verlag Chemie) 318, Günther Siebert).

Presently-preferred embodiments of the invention are shown in the following examples, but they are not intended to be construed as limitation of the present invention. Throughout the specification, the abbreviations "mg.", "ml." and "°C." mean milligram(s), milliliter(s) and degree centigrade, respectively. Percentages are calculated on the weight per volume basis, and yields are calculated on weight of produced citric acids per weight of consumed normal paraffins. The relationship between part(s) by weight and part(s) by volume is the same as that between gram(s) and milliliter(s).

The ATCC numbers put after the name of yeasts employed in the examples are the respective accession numbers at the American Type Culture Collection, Rockville, MD.

EXAMPLE 1

A culture of *Candida lipolytica* (ATCC No. 20114) is inoculated in 250 parts by volume of a sterilized aqueous medium, containing ammonium chloride (0.4%), potassium dihydrogen phosphate (0.05%), magnesium sulfate (0.05% as heptahydrate), yeast extract (0.1%), calcium carbonates (3%) plus 10 parts by weight of sterilized n-decane, and is incubated under agitation and aeration at 26° C. for 7 days.

200 Parts by volume of the culture broth are adjusted to pH 2 with hydrochloric acid and then centrifuged to separate yeast cells. The culture liquid is neutralized by 5N-sodium hydroxide under heating at 100° C. to give precipitates.

While hot, the precipitates are suction-filtered to obtain totally 12.0 parts by weight (dry weight) of calcium (+)-isocitrate and calcium citrate. In addition a small amount of the calcium salts of citric acids is recovered from the filtrate. The collected calcium salts are suspended in 200 parts by volume of water and a 50% solution of sulfuric acid is added dropwise to the above suspension under stirring until presence of superfluous sulfate is confirmed by addition of barium chloride.

The whole is heated under boiling for about 30 minutes and, while hot, filtered. The filtrate is concentrated to a sirup at a temperature between about 50° to 60° C. under reduced pressure while the precipitated calcium sulfate is filtered off, if it appears.

Separately, 700 parts by weight of chromatographic silica gel are mixed with 500 parts by volume of a 0.5N-sulfuric acid solution and the mixture is suspended in about 5000 parts by volume of chloroform containing 15% of n-butanol. The resulting suspension is packed into a column.

On the other hand, the concentrate prepared above is dissolved in about 40 parts by volume of 0.5N-sulfuric acid, and the solution is admixed with 60 parts by weight of the same chromatographic silica gel as above. The mixture is put on the above prepared column together with a small amount of chloroform. The chloroform is allowed to flow down. After the passage of chloroform through the column is completed, the top of the column is covered with glass wool, onto which are successively poured the following two solutions in that order, if necessary, under pressure.

The said two solutions are prepared by shaking 0.5N sulfuric acid with either one of the two n-butanol-chloroform mixtures, one of which contains 25% of n-butanol and the other contains 35% of n-butanol. By the second eluting solution, two acids fractions are obtained.

Of those two fractions, the latter fraction is washed with water so that all the acids occur in the aqueous solution. The aqueous solution is concentrated under reduced pressure, whereupon 4.6 parts by weight of (+)-isocitric acid is obtained in a sirupy state. In addition 3.4 parts by weight of citric acid is recovered from the former fraction of the above two acid fractions. (Yield of citric acids 100.0%).

EXAMPLE 2

A culture of *Candida lipolytica* (ATCC No. 20114) is inoculated in 250 parts by volume of a sterilized aqueous medium containing ammonium chloride (0.4%), potassium dihydrogen phosphate (0.05%), magnesium sulfate heptahydrate (0.05%), yeast extract (0.1%), n-hexadecane (4%), calcium chloride dihydrate (0.01%) plus 0.0025 part by weight of bromocresol green, and is incubated under agitation and aeration at 28° C. for 8 days.

During the incubation, the pH of the culture medium is adjusted with a 5% solution of calcium hydroxide so as to keep the color of the medium green. 200 Parts by volume of thus-obtained culture broth is subjected to further recovering procedures as in Example 1 to give 6.4 parts by weight of citric acid and 3.8 parts by weight of (+)-isocitric acid. (Yield of citric acids 127.5%).

EXAMPLE 3

A culture of *Candida tropicalis* (ATCC No. 20115) is inoculated in 250 parts by volume of a sterilized aqueous medium containing ammonium sulfate (0.4%), potassium dihydrogen phosphate (0.1%), magnesium sulfate heptahydrate (0.1%), ferric sulfate heptahydrate (0.001%), calcium chloride (0.01%), manganese sulfate tetrahydrate (0.001%), yeast extract (0.05%), n-tetradecane (5%) (pH 5.0), and incubated under agitation and aeration at 28° C. for 8 days while the pH of the culture broth is being kept at 5.0 with sodium hydroxide. At the end of the incubation period, 16.7 mg. of citric acid and 4.3 mg. of (+)-isocitric acid per ml. of the broth are accumulated.

EXAMPLE 4

A culture of *Candida intermedia* (ATCC 20178) is inoculated in 250 parts by volume of a sterilized aqueous medium containing ammonium sulfate (0.4%), potassium dihydrogen phosphate (0.05%), magnesium sulfate heptahydrate (0.05%), yeast extract (0.1%), calcium carbonate (3%) and distilled component (petroleum fraction) including 82% of n-paraffins with 12 to 16 carbon atoms in the molecule (5%), and is incubated under agitation and aeration at 30° C. for 6 days. At the end of the incubation period, 12.4 mg. of citric acid and 6.0 mg. of (+)-isocitric acid per ml. of the culture broth are accumulated.

EXAMPLE 5

A culture of *Candida parapsilosis* (ATCC No. 20179) is inoculated in 250 parts by volume of a sterilized medium containing the same components as in Example 1 plus calcium acetate (1%) and 10 parts by weight of distilled fraction including n-paraffins with 16 to 20 carbon atoms in the molecule, and is incubated under agitation and aeration for 8 days. At the end of the incubation period, 18.1 mg. of citric acid and 2.4 mg. of (+)-isocitric acid per ml. of culture broth are accumulated.

EXAMPLE 6

In the same manner as in Example 2, 18.4 mg. of citric acid and 7.8 mg. of (+)-isocitric acid per ml. of the culture broth are accumulated by the incubation of *Candida quilliermondii* (ATCC No. 20118).

EXAMPLE 7

A culture of *Candida brumptii* (ATCC No. 20117) is inoculated in 300 parts by volume of a sterilized aqueous medium, containing ammonium chloride (0.2%), potassium dihydrogen phosphate (0.1%), magnesium sulfate (0.05% as heptahydrate), yeast extract (0.1%) plus 18 parts by weight of sterilized n-hexadecane and 12 parts by weight of sterilized calcium carbonate, and is incubated under agitation and aeration at 26° to 28° C. for 4 days.

At the end of which period, 30 mg. of (+)-isocitric acid per ml. of the broth is accumulated. No citric acid is detected.

The resulting broth is adjusted to pH 2.0 with 3N-HCl and centrifuged, whereby the yeast cells are separated from the acidic liquor. The cells are suspended in a small amount of water whereby they are washed. The washing is combined with the acidic liquor, and after the combined solution is adjusted to pH 6.8 with 5N-NaOH, it is heated at 100° C. for 30 minutes, whereby sediments are formed. When hot, they are suction-filtered, whereupon 11.7 parts by weight (air-dried weight) of calcium (+)-isocitrate are obtained. In this instance, since a small amount of (+)-isocitrate remains dissolved in the filtrate, the filtrate is concentrated under reduced pressure to about one-third of the initial volume and the concentrate is treated in the same manner as above to recover some calcium (+)-isocitrate. The total amount of the calcium salt obtained as above is then dissolved in about 660 parts by volume of cold water and the solution is passed through a column impregnated with 150 parts by volume of Amberlite IR-120 (H+type), whereby the calcium ion is completely removed. The resulting aqueous solution of (+)-isocitric acid is treated with activated carbon when cold, and concentrated under reduced pressure until it becomes a rather watery sirup. The concentrate is allowed to stand in a desiccator, whereupon about 7.8 parts by weight of (+)-isocitric acid is obtained.

A portion of the acid is heated on boiling water bath under reduced pressure so that it foams and gradually solidifies. Then, it is dissolved in warm ethyl acetate, and chloroform is added dropwise until the solution becomes turbid. The turbid solution is then allowed to stand overnight in an ice room. The above procedure yields an approximately theoretical amount of the lactone body of (+)-isocitric acid.

EXAMPLE 8

A culture of Candida sp. (ATCC No. 20180) is inoculated in 150 parts by volume of a sterilized tap water solution, containing ammonium chloride (0.2%), potassium dihydrogen phosphate (0.1%) magnesium sulfate (0.1%) as hepta hydrate), yeast extract (0.1%) plus 6 parts by weight of sterilized (I) n-tetradecane or (II) decane, and incubated in the same manner as in Example 7 for 4 days.

At the end of which period, 28 mg. of (+)-isocitric acid per ml. of the broth is accumulated in case of tetradecane being used as a carbon source, on the other hand, 22 mg. of (+)-isocitric acid per ml. of the broth is accumulated in case of decane, but no citric acid is detected in both cases.

The culture broth is suction-filtered with diatom earth as filter aid. The solid fraction which consists mainly of yeast cells is washed with a small amount of cold water.

The washing and the above obtained filtrate are combined and admixed with about an equal amount of methanol, and the mixture is left standing until sediments are formed to a full extent. Successive to separation by suction-filtration, the sediments are treated in the same manner as in Example 7, whereby (+)-isocitric acid is recovered in an approximately theoretical amount.

EXAMPLE 9

A culture of *Candida parapsilosis* (ATCC No. 20181) is inoculated in the same medium as employed in Example 7 and incubated in the same manner, whereby 9 mg. of (+)-isocitric acid and 4.2 mg. of citric acid per ml. of the resulting broth are formed at the same time. From 100 parts by volume of the broth, 0.52 part by weight of (+)-isocitric acid and 0.18 part by weight of citric acid are obtained.

EXAMPLE 10

A culture of *Candida lipolytica* (ATCC No. 20182) is inoculated in a 150 parts by volume of a sterilized tap water solution containing ammonium chloride (0.2%), potassium dihydrogen phosphate (0.05%), magnesium sulfate (0.05% as heptahydrate) and yeast extract (0.1%) (pH 6.0) plus 6 parts by weight of sterilized calcium plus 6 parts by weight of sterilized (I) tetradecane or (II) hexadecane, and incubated for 5 days in the same manner as in Example 7. The resulting broths contain 1% of (+)-isocitric acid where tetradecane is used as the source of carbon, and 1.3% where hexadecane is the carbon source.

At the same time, citric acid is also produced in a yield of 0.9% where the carbon source is tetradecane and 1.3% in the case of hexadecane.

What is claimed is:

1. A method for producing (+)-isocitric acid which comprises inoculating a (+)-isocitric acid-accumulating and hydrocarbon-assimilating strain of a yeast belonging to the genus Candida in an aqueous culture medium containing at least one normal paraffin containing 9 to 20 carbon atoms in the molecule as the main carbon source; incubating the culture at a pH of from about 4 to about 7.5 until (+)-isocitric acid is substantially accumulated in the culture broth; and separating the so-accumulated (+)-isocitric acid therefrom.

2. A method according to claim 1, wherein the incubation temperature is between 15° and 40° C.

3. A method according to claim 1, wherein the pH of the culture medium is maintained between 5 and 6.5.

4. A method according to claim 1, wherein the yeast is *Candida lipolytica*.

5. A method according to claim 1, wherein the yeast is *Candida tropicalis*.

6. A method according to claim 1, wherein the yeast is *Candida intermedia*.

7. A method according to claim 1, wherein the yeast is *Candida parapsilosis*.

8. A method according to claim 1, wherein the yeast is *Candida quilliermondii*.

9. A method according to claim 1, wherein the yeast is *Candida brumptii*.

10. A method according to claim 1, wherein the yeast is Candida sp. (ATCC 20180).

11. A method according to claim 4, wherein the yeast is *Candida lipolytica* (ATCC 20114).

12. A method according to claim 4, wherein the yeast is *Candida lipolytica* (ATCC 20182).

13. A method according to claim 5, wherein the yeast is *Candida tropicalis* (ATCC 20115).

14. A method according to claim 6, wherein the yeast is *Candida intermedia* (ATCC 20178).

15. A method according to claim 7, wherein the yeast is *Candida parapsilosis* (ATCC 20179).

16. A method according to claim 7, wherein the yeast is *Candida parapsilosis* (ATCC 20181).

17. A method according to claim 8, wherein the yeast is *Candida quilliermondii* (ATCC 20118).

18. A method according to claim 9, wherein the yeast is *Candida brumptii* (ATCC 20117).

19. A method according to claim 1, wherein the pH is maintained at from about 4 to about 7.5 during the course of the incubation by the addition of a pH-adjusting agent.

20. A method according to claim 19 wherein said pH-adjusting agent comprises a member of the group of alkalai metal salts, alkaline earth metal salts, ammonium salts, alkali metal hydroxides, alkaline earth metal hydroxides, and ammonium hydroxide.

21. A method according to claim 19, wherein the pH-adjusting agent is calcium carbonate, calcium acetate, sodium hydroxide, calcium hydroxide or aqueous ammonia.

22. A method according to claim 19, wherein the pH is maintained at from about 5 to about 6.5.

23. A method according to claim 1, wherein the culture is incubated in the presence of calcium ions or magnesium ions.

24. A method according to claim 1, wherein said aqueous culture medium also contains a second carbon source.

25. A method according to claim 23, wherein the second carbon source is a carbohydrate.

26. A method for producing citric acid and (+)-isocitric acid, which comprises inoculating a citric and (+)-isocitric acids-accumulating and hydrocarbon-assimilating strain of a yeast belonging to the genus Candida, in an aqueous culture medium containing at least one normal paraffin containing 9 to 20 carbon atoms in the molecule as a main carbon source; incubating the culture at a pH of from about 4 to about 7.5 until citric acid and (+)-isocitric acid are substantially accumulated in the culture medium, and separating the so-accumulated citric acid and (+)-isocitric acid therefrom.

27. A method for producing (+)-isocitric acid, which comprises inoculating a (+)-isocitric acid-accumulating and hydrocarbon-assimilating strain of a yeast belonging to the genus Candida, in an aqueous culture medium containing at least one normal paraffin containing 9 to 20 carbon atoms in the molecule as a main carbon source; incubating the culture under conditions of pH and temperature such that (+)-isocitric acid is accumulated, for a time until (+)-isocitric acid is substantially accumulated in the culture medium, and separating the so-accumulated (+)-isocitric acid form the culture medium.

28. A method according to claim 27, wherein the pH is maintained at a level at which (+)-isocitric acid is accumulated by the addition of a pH adjusting agent.

29. A method according to claim 27, wherein said pH adjusting agent comprises a member of the group of alkali metal salts, alkaline earth metal salts, ammonium salts, alkali metal hydroxides, alkaline earth metal hydroxides, and ammonium hydroxide.

30. A method according to claim 27, wherein the yeast is *Candida lipolytica, Candida tropicalis, Candida intermedia, Candida parapsilosis,* or *Candida guilliermondii*.

31. A method according to claim 27, wherein the yeast is *Candida lipolytica*.

32. A method according to claim 31, wherein the yeast is *Candida lipolytica* (ATCC 20114).

33. A method according to claim 31, wherein the yeast is *Candida lipolytica* (ATCC 20182).

34. A method according to claim 27, wherein the yeast is a citric and (+)-isocitric acids-accumulating and hydrocarbon-assimilating strain of a yeast belonging to the genus Candida, said incubation is conducted until citric acid and (+)-isocitric acids are substantially accumulated in the culture medium, and further comprising separating the so-accumulated citric acid from the culture medium.

* * * * *

UNITED STATES PATENT AND TRADEMARK OFFICE
CERTIFICATE OF CORRECTION

PATENT NO. : 4,391,908

DATED : July 5, 1983

INVENTOR(S) : Takeshi Tabuchi; Matazo Abe

It is certified that error appears in the above—identified patent and that said Letters Patent is hereby corrected as shown below:

On the cover sheet of United States Patent 4,391,908, left column, item [30] - Foreign Application Priority Data, line one: change "52-36391" to "42-36391"

Line two: change "52-79802" to "42-79892"

Column 3, line 26: change "27" to "27".

Signed and Sealed this

Twenty-first Day of February 1984

[SEAL]

Attest:

Attesting Officer

GERALD J. MOSSINGHOFF

Commissioner of Patents and Trademarks